United States Patent [19]

Haywood et al.

[11] Patent Number: 4,480,786

[45] Date of Patent: Nov. 6, 1984

[54] HUMIDIFIER, VAPORIZER AND ROOM FRESHENER

[76] Inventors: Ronald S. Haywood, 1273 SE. Second Terrace, P.O. Box 8647, Deerfield Beach, Fla. 33441; Melvin L. Landini, 73 Hutchinson Ave., Hawthorne, N.J. 07576

[21] Appl. No.: 494,903

[22] Filed: May 16, 1983

[51] Int. Cl.³ .............................................. F24F 3/14
[52] U.S. Cl. ................................. 237/78 R; 126/113
[58] Field of Search .......................... 237/78 A, 78 B; 126/113; 62/304

[56] References Cited

U.S. PATENT DOCUMENTS

| | | | |
|---|---|---|---|
| 1,014,229 | 1/1912 | Kelsey . | |
| 1,192,020 | 7/1916 | Tweed | 137/200 |
| 1,464,110 | 8/1923 | Ramsey | 237/17 R |
| 2,083,690 | 10/1935 | Cohen | 237/78 |
| 2,212,996 | 8/1940 | Weeks | 237/78 |
| 2,244,017 | 6/1941 | Maxwell | 237/78 |
| 2,395,512 | 2/1936 | Skilbeck | 237/78 |
| 2,416,885 | 3/1947 | Skilbeck | 237/78 |
| 2,446,665 | 8/1948 | Rozner | 261/25 |
| 2,515,310 | 7/1950 | Messina | 21/118 |
| 2,535,772 | 12/1950 | Woolley | 237/78 |
| 2,605,970 | 8/1952 | Leavie | 237/78 |

FOREIGN PATENT DOCUMENTS

| | | | |
|---|---|---|---|
| 400839 | 4/1933 | United Kingdom | 237/78 |
| 352448 | 9/1937 | Italy | 237/78 |

Primary Examiner—Albert J. Makay
Assistant Examiner—Henry Bennett
Attorney, Agent, or Firm—Gottlieb, Rackman & Reisman

[57] ABSTRACT

There is disclosed a humidifier having application as a vaporizer for use in line with a steam heating system. The humidifier includes an outer casing and inner receptacle which divides the casing into outer humidifying and inner vaporizing chambers arranged in telescoping and spaced relation. The outer chamber includes a steam inlet opening for connecting the humidifier to the heating system. The inner chamber includes an exteriorly disposed steam venting opening for emission of steam vapor. A valve including a plurality of apertures in the inner receptacle regulates venting of steam vapor through the venting opening. In application of the humidifier as a vaporizer, a volatile fluid is received in the inner chamber for controlled vaporization and dispersal.

6 Claims, 4 Drawing Figures

HUMIDIFIER, VAPORIZER AND ROOM FRESHENER

DESCRIPTION

1. Technical Field

This invention relates to a humidifying device for use in a steam radiator heating system and, more particularly to a humidifying device having application for use as a vaporizer and room freshener.

2. Background Art

Humidifying and vaporizing devices designed for operation in line with steam heating systems are generally well known in the prior art. These devices are commonly designed to replace standard air exhaust valves employed for venting steam radiators. Such humidifying devices are exemplified by U.S. Pat. Nos. 2,535,772 to Woolley and 2,395,512 to Skilbeck.

Prior art humidifying devices often incorporate humidifying chambers and valve venting mechanisms. In general, difficulties in known devices have been presented by their employment of complicated steam venting structures to obtain the regulated dispersement of steam vapor. The Woolley patent, for example, employs an elaborate venting structure including a needle and ball valve arrangement which coacts with a flotation device. Provision of such complicated arrangements of movable parts permits malfunctioning of the humidifier by reason of wear of the parts, and jamming of valve members, resulting in a device which is not entirely satisfactory from the standpoint of operational reliability and efficiency. Additionally, utilization of such elaborate component structures, requires precise adherence to specification tolerances in the manufacturing process, considerably increasing manufacturing costs.

In other respects, prior art humidifiers fail to satisfactorily provide for the drainage and return of condensation from the humidifying device to the steam heating system. The Woolley patent shows a nipple conduit extending from a humidifying chamber to the steam heating system. A baffle member divides the nipple into separate conduits for flow of condensation and steam vapor. Difficulties are presented with this arrangement where excessive levels of condensation collect in the humidifying device effectively blocking the venting of steam from the radiator.

In the prior art it is also known to provide humidifying devices adapted for application in vaporizing volatile fluids. A device of this type is disclosed in U.S. Pat. No. 2,515,310 to Messina. This patent shows a humidifying chamber which includes a wire mesh basket positioned in line with a venting opening for steam vapor. A pad impregnated with a volatile material, which may be medicinal or aromatic in character, is positioned in the basket for vaporization of the volatile material. Venting of steam vapor is regulated by a manually operated valve structure. Although this patent avoids the complexities of prior art valve arrangements employed in humidifying devices, the vaporizing device does not provide a satisfactory mechanism for regulation of steam vapor vented from the heating system. Such regulation of the steam heating system is necessary in order to avoid rapid depletion of water reserves in the boiler of the heating system and resultant failure of the system.

From the foregoing, it will be appreciated that there is a need in the art for a humidifying device which obtains regulated dispersal of steam vapor and which has application for employment as a vaporizer. Preferably, such a device should be of uncomplex design to provide manufacturing and operational advantages.

Accordingly, it is the broad object of the present invention to provide an improved humidifying device for use in line with a heating system.

A more specific object of the present invention is to provide a humidifying device having application for use as a vaporizer for controlled dispersal of medicinal and aromatic volatile fluids.

Another object of the invention is to provide a humidifier which obtains operational advantage in the drainage and return of condensation from the humidifier to the steam heating system.

Yet another object of the invention is to provide a humidifier having improved manufacturing advantages by having fewer, less complex parts and precise tolerances than humidifying devices according to the prior art.

DISCLOSURE OF THE INVENTION

These and other objects of the present invention are obtained by providing a humidifying device, including an outer casing and an inner receptacle which divides the casing into an outer humidifying chamber and inner vaporizing chamber. The chambers are arranged in telescoping and spaced relation to define steam channels which extend around the periphery of the inner chamber. The outer chamber includes a steam inlet opening which receives an exteriorly threaded nipple adapted for connection to a radiator of a steam heating system. An inclined base surface is provided in the outer chamber to effect the continuous flow of condensation from the outer chamber through the inlet opening into the radiator. The inner chamber has an exteriorly disposed steam venting opening and valve means, which may include a plurality of spaced apertures, to provide a conduit from the outer steam chamber to the atmosphere. As a further feature of the invention, the inner chamber may include a drainage spout and closure cap.

In the operation of the humidifying device steam vapor passes into the outer chamber from the radiator through the connecting nipple and inlet opening. The outer chamber steam then passes through valve apertures for regulated emission through the steam venting opening of the inner chamber. Provision of an inclined base surface in the outer chamber effects a continuous return flow of condensation from the humidifier to the steam heating system. Advantageously, the humidifier also has application as a vaporizer for uniform dispersal of volatile medicinal and aromatic fluids. In this mode of operation, a volatile fluid is poured into the inner chamber receptacle. Steam vapor in the outer chamber circulates through the steam channels around the periphery of the inner receptacle conducting heat to the volatile materials contained in the inner chamber causing vaporization to commence. Venting of steam vapors through the valve apertures of the inner chamber causes further vaporization of the volatile materials and their uniform dispersal in the atmosphere. The spout and cap arrangement of the inner chamber permit drainage of volatile materials from the humidifying device.

Other objects, aspects, features and advantages of the present invention will be apparent when the detailed description of the preferred embodiment of the invention is considered in conjunction with the drawings, which should be construed in an illustrative and not limiting sense, as follows:

BEST MODE FOR CARRYING OUT THE INVENTION

Figure 1:
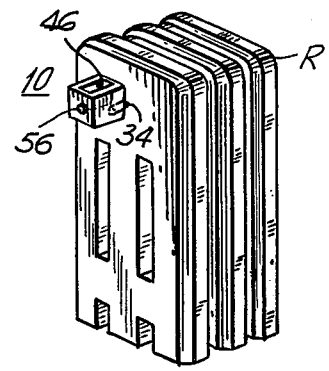
FIG. 1 is a perspective view of a humidifying device according to the present invention shown connected to a steam radiator.
Figure 2:
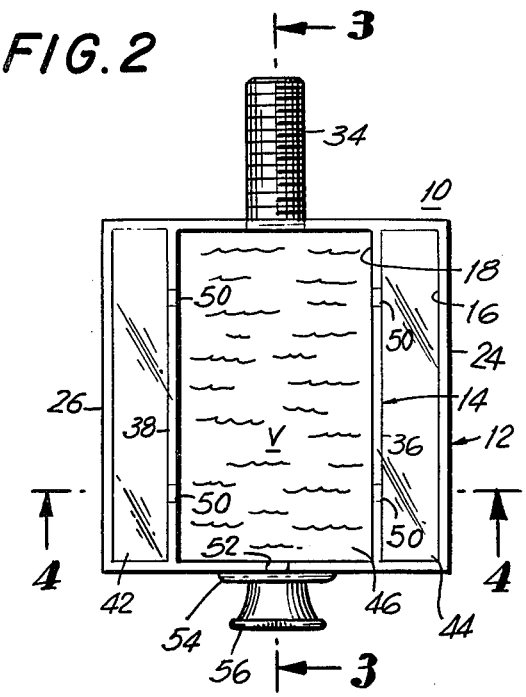
FIG. 2 is a top plan view of the humidifying device containing a volatile fluid in an inner vaporizing chamber.

Referring now to the drawings and, more particularly to FIG. 1 thereof, a humidifying device according to the present invention is generally designated 10. The humidifying device is shown connected to a steam heating radiator R. Although the humidifier has general application for use in steam heating systems, it is advantageously employed as shown in the drawings to replace a conventional air exhaust valve.

The humidifying device 10 comprises an outer casing 12 having an interior receptacle 14 which divides the humidifier 10 into an outer chamber 16 and interior chamber 18. For reasons which will be explained hereinafter, the humidifying and vaporizing chambers are arranged in telescoping and spaced relation to define steam channels 20 which extend between vaporizing and humidifying chambers. The casing 12 and inner receptacle 14 are preferably formed of a thermoconductive synthetic plastic such as a polypropylene or a metal. Employment of synthetic plastics is preferred in that they permit fabrication of the humidifier 10 by injection molding processes.

Figure 3:
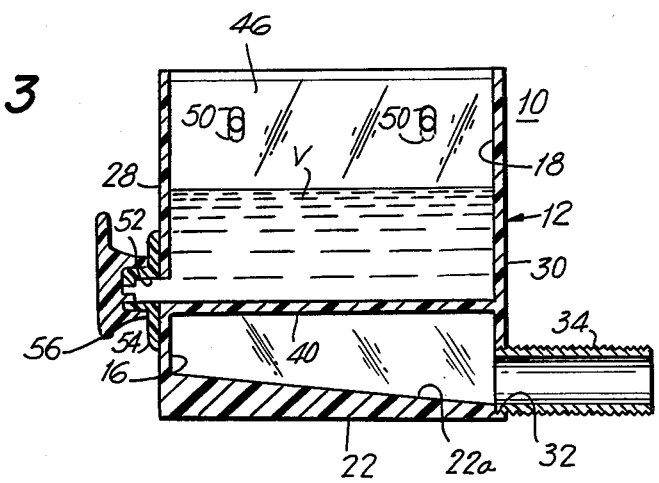
FIG. 3 is a cross-sectional view of the device taken substantially along the line 3—3 of FIG. 2.
Figure 4:
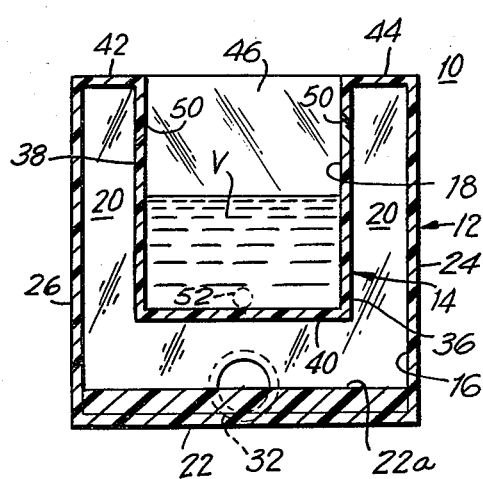
FIG. 4 is a cross-sectional view of the device.

The outer casing 12, best shown in FIGS. 3-4, has a generally cubical configuration including a base 22, upright sidewalls 24, 26 and front and rear walls 28, 30. At the base end of rear wall 30, there is an opening 32 which receives conventional threaded nipple 34 to permit coupling of the humidifier 10 to a steam heating radiator. The nipple 34 may advantageously be fabricated as an integral component of the humidifier 10 as previously described by injection molding processes. Alternatively, the opening 32 may be internally threaded for receiving a separate component nipple which may be positioned in the opening and sealed at the point of attachment by conventionally known processes.

Referring to FIG. 3, the base surface 22 of the outer casing 12 has an inclined interior surface 22a extending from the front wall 28 to the rear wall 30, the lower end being in line and adjacent to the opening 32 and nipple 34. In operation of the humidifying device 10, this arrangement provides for the continuous return flow of condensation from the unit to the steam heating system.

The inner receptacle 14 which defines vaporizing chamber 18 includes sidewalls 36, 38, a base 40, top panel sections 42, 44 and an open steam venting top 46. The inner receptacle sidewalls 36, 38 are spaced inwardly from corresponding outer casing sidewalls 24, 26 to define steam channels 20. In like manner, the receptacle base 40 is spaced from outer casing base 22 to define the humidifying chamber 16. As shown best in FIG. 4, the humidifying chamber 16 is contiguous with the steam channels 20. This arrangement permits steam vapor in the humidifying chamber 16 to circulate around the periphery of the receptacle 14 and conduct heat to the inner vaporizing chamber 18.

For purposes of regulating the discharge of steam vapor from the radiator R through the steam venting opening 46, the humidifier also includes a valve means which may comprise a plurality of apertures in the receptacle sidewalls 36, 38. In the preferred embodiment of the humidifier, the valve means includes a pair of spaced apertures 50 positioned in each of the receptacle sidewalls, each aperture having a diameter in cross section in the range of 1/16th of an inch. As shown in FIG. 3, the apertures 50 are disposed angularly inwardly so that steam vapor passing from the humidifying chamber 16 through the venting opening 46 is directed upwardly to effect its efficient discharge from the humidifier.

As a further feature of the humidifying device 10, there is provided an outlet opening in the vaporizing chamber 18 which extends through the front exterior casing wall 28, see FIG. 3. The outlet opening 52 includes a spout 54 attached to the exterior surface of the casing wall 28 and a closure cap 56 which permit drainage of fluids from the vaporizing chamber 18.

OPERATION OF THE HUMIDIFYING DEVICE

The humidifying device 10 of the present invention has application for use generally with steam heating systems and may be connected to conduits in such systems as, for example, riser pipes, or as shown in FIG. 1 may be employed to replace a radiator air exhaust valve. As will be described hereinafter the humidifier has application for use as a vaporizer and room freshener.

When employed as a humidifier, steam vapor passes into the humidifying chamber 16 through the connecting nipple 34 and inlet opening 32 and then into the surrounding atmosphere through the venting opening 46. The valve apertures 50 in the sidewalls 36, 38 of the interior receptacle function to regulate the emission of steam vapor, avoiding excessive depletion of water reserves from the steam heating system. Provision of an inclined interior base surface 22a in the outer humidifying chamber effects continuous return flow of condensation from the humidifying device to the steam heating system. This feature provides particular advantage in the operation of the humidifier 10 by avoiding excessive collection of condensation within the humidifying chamber, blockage of the inlet opening 32 and resultant malfunctioning of the humidifier.

The humidifier 10 also has application as a vaporizer for dispersal of volatile medicinal and aromatic fluids, designated V in drawings. In this mode of operation, the volatile fluid is poured into the vaporizing chamber 18 through the ventilation opening 46. Steam vapor entering the outer humidifying chamber 16 from the steam heating system circulates within the humidifying chamber 16 and steam channels 20, surrounding the periphery of the steam receptacle and vaporizing chamber, thereby conducting heat through the receptacle to cause vaporization of the volatile fluid. Additionally, steam vapor passes through the steam regulating apertures 50 to effect further vaporization of the volatile fluid and its efficient dispersal into the atmosphere through venting opening 46. The spout and cap closure 54, 56 of the interior vaporization chamber permit ready drainage of volatile fluids from the humidifying device.

From the foregoing, it will be appreciated that the present invention provides a humidifying device, particularly useful in line with steam radiators in place of conventional air exhaust valves which overcomes the difficulties of the prior art and achieves the objects stated heretofore. In particular, there is disclosed a humidifier of uncomplex design which provides efficiency in operation and improved manufacturing advantages.

Numerous modifications may be possible in light of the above teachings. For example, through the humidifier 10 is illustrated as having a cubicle configuration, the features of the invention may be incorporated in other geometric configurations. Similarly, although the inclined base surface 22a of the outer casing 12 is generally planar, other surface contours may be employed to direct the return flow of condensation to the steam heating system. By way of example, there may be provided an inclined channel in base surface 22a which feeds into the inlet opening and nipple 32, 34. It is to be understood, therefore, that the above-described embodiment of the invention is merely illustrative and that other embodiments may be devised by those skilled in the art, without departing from the spirit or scope of the present invention, as set forth in the appended claims.

We claim:

1. A device for use in line with a steam heating radiator having application as a humidifier and a vaporizer for dispersal of volatile fluids, comprising:
   an outer chamber having a steam inlet opening;
   means for connecting said inlet opening to the steam radiator for passage of steam vapor into said outer chamber, said connecting means including a nipple secured in said inlet opening;
   an inner chamber having a steam venting opening, said inner chamber being disposed in telescoping relation within said outer chamber;
   said outer and inner chambers being spaced apart to define a steam channel between said chambers, said steam channel extending around the periphery of said inner chamber;
   valve means for regulating discharge of steam from the radiator through said steam venting opening, said valve means comprising a plurality of spaced apertures in said inner chamber; and
   means for continuously draining steam condensation from said outer chamber to the radiator, said drainage means including an inclined base surface in said outer chamber;
   the device being operable in a first mode as a humidifier by regulation of the emission of steam vapor from the steam radiator system through the steam venting opening, the device being operable in a second mode as a vaporizer when volatile fluids are received in said inner chamber for controlled vaporization by steam vapor.

2. A device for use in line with a steam heating radiator having application as a humidifier and a vaporizer for dispersal of volatile fluids, comprising:
   an outer casing;
   an inner receptacle disposed in telescoping relation within said casing to divide the casing into an outer humidifying chamber and inner vaporizing chamber;
   said outer and inner chambers being spaced apart to define a steam channel between said chambers, said steam channel extending around the periphery of said inner chamber;
   said outer casing having a steam inlet opening;
   said inner receptacle having a steam venting opening;
   means for connecting said inlet opening to the steam radiator for passage of steam vapor into said outer chamber, said connecting means including a nipple secured in said inlet opening;
   valve means for regulating discharge of steam from the radiator through said steam venting opening, said valve means comprising a plurality of spaced apertures in said inner receptacle; and
   means for continuously draining steam condensation from said outer chamber to the radiator, said drainage means including an inclined base surface in said outer casing;
   the device being operable in a first mode as a humidifier by regulation of the emission of steam vapor from the steam radiator system through the steam venting opening, the device being operable in a second mode as a vaporizer when volatile fluids are received in said inner chamber for controlled vaporization by steam vapor.

3. A device as set forth in claim 1 further comprising an outlet means for drainage of volatile fluids from said inner chamber, said outlet means including a spout secured to an exteriorly disposed wall of said inner chamber and a closure cap.

4. A device as set forth in claim 1, wherein said valve means includes four spaced apertures, said apertures having cross-sectional diameters in the range of 1/16th of an inch.

5. A device as set forth in claim 2 further comprising an outlet means for drainage of volatile fluids from said inner chamber, said outlet means including a spout secured to an exteriorly disposed wall of said inner chamber and a closure gap.

6. A device as set forth in claim 2, wherein said valve means includes four spaced apertures, said apertures having cross-sectional diameters in the range of 1/16th of an inch.

* * * * *